United States Patent [19]

Peery et al.

[11] Patent Number: 6,071,724

[45] Date of Patent: Jun. 6, 2000

[54] *STREPTOCOCCUS PNEUMONIAE* GENE SEQUENCE ERA

[75] Inventors: Robert Brown Peery, Brownsburg; Michele Louise Young Bellido; Genshi Zhao, both of Indianapolis, all of Ind.

[73] Assignee: Eli Lilly and Company, Indianapolis, Ind.

[21] Appl. No.: 08/986,765

[22] Filed: Dec. 8, 1997

Related U.S. Application Data

[60] Provisional application No. 60/036,281, Dec. 13, 1996.

[51] Int. Cl.⁷ ........................................ C12P 21/06
[52] U.S. Cl. .................... 435/69.3; 435/320.1; 435/69.1; 435/71.1; 435/71.2; 435/440; 435/471; 435/252.3; 435/254.11; 435/257.2; 435/822; 536/23.1; 536/23.7; 536/24.32
[58] Field of Search .............................. 435/320.1, 69.1, 435/69.3, 71.1, 71.2, 440, 471, 252.3, 254.11, 257.2, 822; 536/23.1, 23.7, 24.32

[56] References Cited

PUBLICATIONS

Song et al. 1989, Mol. Gen. Genet. 216: 462–468.
Yamashita et al. 1993, J. Bacteriol, 175(19):6220–6228.
Lindler et al. 1987, J. Bacteriol. 169(7):3199–3208.
Stratagene, 1991 Product Catalogue, p. 292.
Boehringer Mannheim Biochemicals 1991, catalog p. 557.
Promega, 1993/4 catalog pp. 90–91.
New England Biolabs Catalog 1986/7 pp. 60–62.

*Primary Examiner*—Christopher L. Chin
*Assistant Examiner*—Jennifer Graser
*Attorney, Agent, or Firm*—Raymond S. Parker III; Thomas D. Webster

[57] ABSTRACT

The invention provides isolated nucleic acid compounds encoding Era of *Streptococcus pneumoniae*. Also provided are vectors and transformed host cells for expressing the encoded protein, and a method for identifying compounds that bind and/or inhibit said protein.

12 Claims, No Drawings

STREPTOCOCCUS PNEUMONIAE GENE SEQUENCE ERA

BACKGROUND OF THE INVENTION

This application claims the benefit of U.S. Provisional Application No. 60/036,281, filed Dec. 13, 1996.

This invention provides isolated DNA sequences, proteins encoded thereby, and methods of using said DNA and protein in a variety of applications.

Widespread antibiotic resistance in common pathogenic bacterial species has justifiably alarmed the medical and research communities. Frequently, resistant organisms are co-resistant to several antibacterial agents. Penicillin resistance in *Streptococcus pneumoniae* has been particularly problematic. This organism causes upper respiratory tract infections. Modification of a penicillin-binding protein (PBP) underlies resistance to penicillin in the majority of cases. Combating resistance to antibiotic agents will require research into the molecular biology of pathogenic organisms. The goal of such research will be to identify new antibacterial agents. While researchers continue to develop antibiotics effective against a number of microorganisms, Streptococcus pneumoniae has been more refractory. In part, this is because *Streptococcus pneumoniae* is highly recombinogenic and readily takes up exogenous DNA from its surroundings.

Thus, there is a need for new antibacterial compounds and new targets for antibacterial therapy in Streptococcus pneumoniae.

BRIEF SUMMARY OF THE INVENTION

The present invention relates to an isolated gene and encoded protein from *S. pneumoniae*. The invention enables: (1) preparation of probes and primers for use in hybridizations and PCR amplifications, (2) production of proteins and RNAs encoded by said gene and related nucleic acids, and (3) methods to identify compounds that bind and/or inhibit said protein(s).

In one embodiment the present invention relates to an isolated nucleic acid molecule encoding an Era protein.

In another embodiment, the invention relates to a nucleic acid molecule comprising the nucleotide sequence identified as SEQ ID NO:1 or SEQ ID NO:3.

In another embodiment, the present invention relates to a nucleic acid that encodes SEQ ID NO:2.

In another embodiment the present invention relates to an isolated protein molecule, wherein said protein molecule comprises the sequence identified as SEQ ID NO:2.

In yet another embodiment, the present invention relates to a recombinant DNA vector that incorporates the Era gene in operable linkage to gene expression sequences enabling the gene to be transcribed and translated in a host cell.

In still another embodiment the present invention relates to host cells that have been transformed or transfected with the cloned Era gene such that said gene is expressed in the host cell.

This invention also provides a method of determining whether a nucleic acid sequence of the present invention, or fragment thereof, is present in a sample, comprising contacting the sample, under suitable hybridization conditions, with a nucleic acid probe of the present invention.

In a still further embodiment, the present invention relates to a method for identifying compounds that bind and/or inhibit the Era protein.

DETAILED DESCRIPTION OF THE INVENTION

"ORF" (i.e. "open reading frame") designates a region of genomic DNA beginning with a Met or other initiation codon and terminating with a translation stop codon, that potentially encodes a protein product. "Partial ORF" means a portion of an ORF as disclosed herein such that the initiation codon, the stop codon, or both are not disclosed.

"Consensus sequence" refers to an amino acid or nucleotide sequence that may suggest the biological function of a protein, DNA, or RNA molecule. Consensus sequences are identified by comparing proteins, RNAs, and gene homologues from different species.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

"Essential genes" or "essential ORFs" or "essential proteins" refer to genomic information or the protein(s) or RNAs encoded thereby, that when disrupted by knockout mutation, or by other mutation, result in a loss of viability of cells harboring said mutation.

"Non-essential genes" or "non-essential ORFs" or "non-essential proteins" refer to genomic information or the protein(s) or RNAs encoded therefrom which when disrupted by knockout mutation, or other mutation, do not result in a loss of viability of cells harboring said mutation.

"Minimal gene set" refers to a genus comprising about 256 genes conserved among different bacteria such as M. genitalium and H. influenzae. The minimal gene set may be necessary and sufficient to sustain life. See e.g. A. Mushegian and E. Koonin, "A minimal gene set for cellular life derived by comparison of complete bacterial genomes" Proc. Nat. Acad. Sci. 93, 10268-273 (1996).

"Knockout mutant" or "knockout mutation" as used herein refers to an in vitro engineered disruption of a region of native chromosomal DNA, typically within a protein coding region, such that a foreign piece of DNA is inserted within the native sequence. A knockout mutation occurring in a protein coding region prevents expression of the wild-type protein. This usually leads to loss of the function provided by the protein. A "knockout cassette" refers to a fragment of native chromosomal DNA having cloned therein a foreign piece of DNA that may provide a selectable marker.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refer to the capacity of purine and pyrimidine nucleotides to associate through hydrogen bonding to form double stranded nucleic acid molecules. The following base pairs are related by complementarity: guanine and cytosine; adenine and thymine; and adenine and uracil. As used herein, "complementary" applies to all base pairs comprising two single-stranded nucleic acid molecules. "Partially complementary" means one of two single-stranded nucleic acid molecules is shorter than the other, such that one of the molecules remains partially single-stranded.

"Oligonucleotide" refers to a short nucleotide chain comprising from about 2 to about 25 nucleotides.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which can be used to hybridize with another nucleic acid compound.

The term "hybridization" or "hybridize" as used herein refers to the process by which a single-stranded nucleic acid molecule joins with a complementary strand through nucleotide base pairing.

"Substantially purified" as used herein means a specific isolated nucleic acid or protein, or fragment thereof, in which substantially all contaminants (i.e. substances that differ from said specific molecule) have been separated from said nucleic acid or protein. For example, a protein may, but not necessarily, be "substantially purified" by the IMAC method as described herein.

"Selective hybridization" refers to hybridization under conditions of high stringency. The degree of hybridization between nucleic acid molecules depends upon, for example, the degree of complementarity, the stringency of hybridization, and the length of hybridizing strands.

The term "stringency" relates to nucleic acid hybridization conditions. High stringency conditions disfavor non-homologous base pairing. Low stringency conditions have the opposite effect. Stringency may be altered, for example, by changes in temperature and salt concentration. Typical high stringency conditions comprise hybridizing at 50° C. to 65° C. in 5× SSPE and 50% formamide, and washing at 50° C. to 65° C. in 0.5× SSPE; typical low stringency conditions comprise hybridizing at 35° C. to 37° C. in 5× SSPE and 40% to 45% formamide and washing at 42° C. in 1×–2× SSPE.

"SSPE" denotes a hybridization and wash solution comprising sodium chloride, sodium phosphate, and EDTA, at pH 7.4. A 20× solution of SSPE is made by dissolving 174 g of NaCl, 27.6 g of NaH2PO4.H2O, and 7.4 g of EDTA in 800 ml of H2O . The pH is adjusted with NaOH and the volume brought to 1 liter.

"SSC" denotes a hybridization and wash solution comprising sodium chloride and sodium citrate at pH 7. A 20× solution of SSC is made by dissolving 175 g of NaCl and 88 g of sodium citrate in 800 ml of H2O . The volume is brought to 1 liter after adjusting the pH with 10N NaOH.

DETAILED DESCRIPTION OF THE INVENTION

The Era gene disclosed herein (SEQ ID NO:1 and SEQ ID NO:4) and related nucleic acids, for example SEQ ID NO:3, encode a GTP-binding GTPase that may be involved in cell division, energy metabolism, and DNA synthesis.

Cells that carry knockout mutations in Era are nonviable. The Era protein is a "minimal gene set" counterpart. The minimal gene set proteins are thought to be essential for viability and are useful targets for the development of new antibacterial compounds.

In one embodiment, the proteins of this invention are purified, and used in a screen to identify compounds that bind and/or inhibit the activity of said proteins. A variety of suitable screens are contemplated for this purpose. For example, the protein(s) can be labeled by known techniques, such as radiolabeling or fluorescent tagging, or by labeling with biotin/avidin. Thereafter, binding of a test compound to a labeled protein can be determined by any suitable means, well known to the skilled artisan.

Skilled artisans will recognize that the DNA molecules of this invention, or fragments thereof, can be generated by general cloning methods. PCR amplification using oligonucleotide primers targeted to any suitable region of SEQ ID NO:1 is preferred. Methods for PCR amplification are widely known in the art. See e.g. PCR Protocols: A Guide to Method and Application, Ed. M. Innis et al., Academic Press (1990) or U.S. Pat. No. 4,889,818, which hereby is incorporated by reference. A PCR comprises DNA, suitable enzymes, primers, and buffers, and is conveniently carried out in a DNA Thermal Cycler (Perkin Elmer Cetus, Norwalk, Conn.). A positive PCR result is determined by, for example, detecting an appropriately-sized DNA fragment following agarose gel electrophoresis.

The DNAs of the present invention may also be produced using synthetic methods well known in the art. (See, e.g., E. L. Brown, R. Belagaje, M. J. Ryan, and H. G. Khorana, Methods in Enzymology, 68:109-151 (1979)). An apparatus such as the Applied Biosystems Model 380A or 380B DNA synthesizers (Applied Biosystems, Inc., 850 Lincoln Center Drive, Foster City, Calif. 94404) may be used to synthesize DNA. Synthetic methods rely upon phosphotriester chemistry [See, e.g., M. J. Gait, ed., Oligonucleotide Synthesis, A Practical Approach, (1984)], or phosphoramidite chemistry.

Protein Production Methods

The present invention relates further to substantially purified proteins encoded by the gene disclosed herein.

Skilled artisans will recognize that proteins can be synthesized by different methods, for example, chemical methods or recombinant methods, as described in U.S. Pat. No. 4,617,149, which hereby is incorporated by reference.

The principles of solid phase chemical synthesis of polypeptides are well known in the art and may be found in general texts relating to this area. See, e.g., H. Dugas and C. Penney, Bioorganic Chemistry (1981) Springer-Verlag, New York, 54–92. Peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

The proteins of the present invention can also be made by recombinant DNA methods. Recombinant methods are preferred if a high yield is desired. Recombinant methods involve expressing the cloned gene in a suitable host cell. The gene is introduced into the host cell by any suitable means, well known to those skilled in the art. While chromosomal integration of the cloned gene is within the scope of the present invention, it is preferred that the cloned gene be maintained extra-chromosomally, as part of a vector in which the gene is in operable-linkage to a promoter.

Recombinant methods can also be used to overproduce a membrane-bound or membrane-associated protein. In some cases, membranes prepared from recombinant cells expressing such proteins provide an enriched source of the protein.
Expressing Recombinant Proteins in Procaryotic and Eucaryotic Host Cells Procaryotes are generally used for cloning DNA sequences and for constructing vectors. For example, the Escherichia coli K12 strain 294 (ATCC No. 31446) is particularly useful for expression of foreign proteins. Other strains of *E. coli*, bacilli such as *Bacillus subtilis*, enterobacteriaceae such as *Salmonella typhimurium* or *Serratia marcescans*, various Pseudomonas species may also be employed as host cells in cloning and expressing the recombinant proteins of this invention. Also contemplated are various strains of Streptococcus and Streptocmyces.

For effective recombinant protein production, a gene must be linked to a promoter sequence. Suitable bacterial promoters include b -lactamase [e.g. vector pGX2907, ATCC 39344, contains a replicon and b -lactamase gene], lactose systems [Chang et al., Nature (London), 275:615 (1978); Goeddel et al., Nature (London), 281:544 (1979)], alkaline phosphatase, and the tryptophan (trp) promoter system [vector pATH1 (ATCC 37695)] designed for the expression of a trpE fusion protein. Hybrid promoters such as the tac promoter (isolatable from plasmid pDR540, ATCC-37282) are also suitable. Promoters for use in bacterial systems also will contain a Shine-Dalgarno sequence, operably linked to the DNA encoding the desired polypeptides. These examples are illustrative rather than limiting.

A variety of mammalian cells and yeasts are also suitable hosts. The yeast Saccharomyces cerevisiae is commonly used. Other yeasts, such as Kluyveromyces lactis, are also suitable. For expression of recombinant genes in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene, a selectable marker for a trp1 mutant.
Purification of Recombinantly-Produced Protein An expression vector carrying a nucleic acid or gene of the present invention is transformed or transfected into a suitable host cell using standard methods. Cells that contain the vector are propagated under conditions suitable for expression of a recombinant protein. For example, if the gene is under the control of an inducible promoter, then suitable growth conditions would incorporate the appropriate inducer. The recombinantly-produced protein may be purified from cellular extracts of transformed cells by any suitable means.

In a preferred process for protein purification a gene is modified at the 5' end, or at some other position, such that the encoded protein incorporates several histidine residues (viz. "histidine tag"). This "histidine tag" enables "immobilized metal ion affinity chromatography" (IMAC), a single-step protein purification method described in U.S. Pat. No. 4,569,794, which hereby is incorporated by reference. The IMAC method enables isolation of substantially pure protein starting from a crude cellular extract.

As skilled artisans will recognize, owing to the degeneracy of the code, the proteins of the invention can be encoded by a large genus of different nucleic acid sequences. This invention further comprises said genus.

The ribonucleic acid compounds of the invention may be prepared using the polynucleotide synthetic methods discussed supra, or they may be prepared enzymatically using RNA polymerase to transcribe a DNA template.

The most preferred systems for preparing the ribonucleic acids of the present invention employ the RNA polymerase from the bacteriophage T7 or the bacteriophage SP6. These RNA polymerases are highly specific, requiring the insertion of bacteriophage-specific sequences at the 5' end of a template. See, J. Sambrook, et al., supra, at 18.82–18.84.

This invention also provides nucleic acids that are complementary to the sequences disclosed herein.

The present invention also provides probes and primers, useful for a variety of molecular biology techniques including, for example, hybridization screens of genomic or subgenomic libraries, or detection and quantification of mRNA species as a means to analyze gene expression. A nucleic acid compound is provided comprising any of the sequences disclosed herein, or a complementary sequence thereof, or a fragment thereof, which is at least 15 base pairs in length, and which will hybridize selectively to *Streptococcus pneumoniae* DNA or mRNA. Preferably, the 15 or more base pair compound is DNA. A probe or primer length of at least 15 base pairs is dictated by theoretical and practical considerations. See e.g. B. Wallace and G. Miyada, "Oligonucleotide Probes for the Screening of Recombinant DNA Libraries," In Methods in Enzymology, Vol. 152, 432–442, Academic Press (1987).

The probes and primers of this invention can be prepared by methods well known to those skilled in the art (See e.g. Sambrook et al. supra). In a preferred embodiment the probes and primers are synthesized by the polymerase chain reaction (PCR).

The present invention also relates to recombinant DNA cloning vectors and expression vectors comprising the nucleic acids of the present invention. Preferred nucleic acid vectors are those that comprise DNA. The skilled artisan understands that choosing the most appropriate cloning vector or expression vector depends on the availability of restriction sites, the type of host cell into which the vector is to be transfected or transformed, the purpose of transfection or transformation (e.g., stable transformation as an extrachromosomal element, or integration into a host chromosome), the presence or absence of readily assayable or selectable markers (e.g., antibiotic resistance and metabolic markers of one type and another), and the number of gene copies desired in the host cell.

Suitable vectors comprise RNA viruses, DNA viruses, lytic bacteriophages, lysogenic bacteriophages, stable bacteriophages, plasmids, viroids, and the like. The most preferred vectors are plasmids.

Host cells harboring the nucleic acids disclosed herein are also provided by the present invention. A preferred host is *E. coli* transfected or transformed with a vector comprising a nucleic acid of the present invention.

The invention also provides a host cell capable of expressing a gene described herein, said method comprising transforming or otherwise introducing into a host cell a recombinant DNA vector comprising an isolated DNA sequence that encodes said gene. The preferred host cell is any strain of *E. coli* that can accommodate high level expression of an exogenously introduced gene. Transformed host cells are cultured under conditions well known to skilled artisans, such that said gene is expressed, thereby producing the encoded protein in the recombinant host cell.

To discover compounds having antibacterial activity, one can look for agents that inhibit cell growth and/or viability by, for example, inhibiting enzymes required for cell wall biosynthesis, and/or by identifying agents that interact with membrane proteins. A method for identifying antibacterial compounds comprises contacting a suitable protein or membrane preparation with a test compound and monitoring by any suitable means an interaction and/or inhibition of a protein of this invention.

For example, the instant invention provides a screen for compounds that interact with the proteins of the invention, said screen comprising:

a) preparing a protein, b) exposing the protein to a test compound; and c) detecting an interaction of said protein with said compound by any suitable means.

The screening method of this invention may be adapted to automated procedures such as a PANDEX® (Baxter-Dade Diagnostics) system, allowing for efficient high-volume screening of compounds.

In a typical screen, a protein is prepared as described herein, preferably using recombinant DNA technology. A test compound is introduced into a reaction vessel containing said protein. The reaction/interaction of said protein and said compound is monitored by any suitable means. For example, binding of a test compound may be carried out by a method disclosed in U.S. Pat. No. 5,585,277, which hereby is incorporated by reference. In this method, binding of a test compound to a protein is assessed by monitoring the ratio of folded protein to unfolded protein, for example, by monitoring sensitivity of said protein to a protease, or amenability to binding of said protein by a specific antibody against the folded state of the protein. For example, a test compound is combined with the Era protein under conditions that cause the protein to exist in a ratio of folded to unfolded states. If the test compound binds the folded state of the protein, the relative amount of folded protein will be higher than in the case of a test compound that does not bind the protein. A similar result would be expected in a control reaction in which test compound is left out of the reaction mix.

In another method, a radioactively-labeled or chemically-labeled compound or protein is used. A specific association between the test compound and protein is monitored by any suitable means.

The following examples more fully describe the present invention. Those skilled in the art will recognize that the particular reagents, equipment, and procedures described are merely illustrative and are not intended to limit the present invention in any manner.

EXAMPLE 1

Production of a Vector for Expressing *S. pneumoniae* Era in a Host Cell

An expression vector suitable for expressing *S. pneumoniae* Era in a variety of procaryotic host cells, such as *E. coli*, is easily made. The vector contains an origin of replication (Ori), an ampicillin resistance gene (Amp) useful for selecting cells which have incorporated the vector following a tranformation procedure, and further comprises the T7 promoter and T7 terminator sequences in operable linkage to the Era coding region. Plasmid pET11A (obtained from Novogen, Madison, Wis.) is a suitable parent plasmid. pET11A is linearized by restriction with endonucleases NdeI and BamHI. Linearized pET11A is ligated to a DNA fragment bearing NdeI and BamHI sticky ends and comprising the coding region of the *S. pneumoniae* Era.

The Era coding region used in this construction is conveniently prepared by PCR amplification from genomic DNA using suitably designed primers. The coding region is slightly modified at the 5' end (amino terminus of encoded protein) in order to simplify purification of the encoded protein product. For this purpose, an oligonucleotide encoding 8 histidine residues is inserted after the ATG start codon at nucleotide position 3 of SEQ ID NO:1. Placement of the histidine residues at the amino terminus of the encoded protein serves to enable the IMAC one-step protein purification procedure.

EXAMPLE 2

Recombinant Expression and Purification of a Protein Encoded by *S. pneumoniae* Era An expression vector that carries the Era gene from the *S. pneumoniae* genome as disclosed herein, and which gene is operably-linked to an expression promoter is transformed into *E. coli* BL21 (DE3)(hsdS gal 1cIts857 ind1Sam7nin5lacUV5-T7gene 1) using standard methods (see Example 4). Transformants, selected for resistance to ampicillin, are chosen at random and tested for the presence of the vector by agarose gel electrophoresis using quick plasmid preparations. Colonies which contain the vector are grown in L broth and the protein product encoded by the vector-borne ORF is purified by immobilized metal ion affinity chromatography (IMAC), essentially as described in U.S. Pat. No. 4,569,794.

Briefly, the IMAC column is prepared as follows. A metal-free chelating resin (e.g. Sepharose 6B IDA, Pharmacia) is washed in distilled water to remove preservative substances and infused with a suitable metal ion [e.g. Ni(II), Co(II), or Cu(II)] by adding a 50 mM metal chloride or metal sulfate aqueous solution until about 75% of the interstitial spaces of the resin are saturated with colored metal ion. The column is then ready to receive a crude cellular extract containing the recombinant protein product.

After removing unbound proteins and other materials by washing the column with any suitable buffer, pH 7.5, the bound protein is eluted in any suitable buffer at pH 4.3, or preferably with an imidizole-containing buffer at pH 7.5.

EXAMPLE 3

Protection of Era from Proteolytic Digestion by Proteinase K

The following are combined and incubated at 54° C. for 5 minutes. Era protein (100 ug/ml), proteinase K (80 ug/ml), 0.1 M Tric-HCl, pH7.5, and test compound at 10-10 to 10-4 M. Samples are removed and undigested Era is quantified by ELISA as follows. Protease incubations are diluted 50-fold with Tris Buffered Saline (TBS). About 50 ul of diluted samples are transferred to ELISA plates and incubated 1 hour at room temperature. The plates are washed with TBS plus 0.1% Tween-20 (TBST). About 50 ul anti-Era rabbit serum diluted 250-fold into TBST plus 5% nonfat dry milk is added to each well and incubated 30 minutes at room temperature. The plate wells are washed again (as above) and 50 ul of goat anti-rabbit IgG alkaline phosphatase conjugate diluted 500-fold in TBST plus 5% nonfat dry milk is added to each well and incubated 30 minutes at room temperature. Wells are washed again and 0.1 ml of 1.0 mg/ml p-nitrophenylphosphate in 0.1% diethanolamine is added. Color development is proportional to alkaline phosphatase antibody conjugate bound.

---

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 900 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..897

(xi) SEQUENCE DESCRIPTION: SEQ ID NO:1:

```
ATG ACT TTT AAA TCA GGC TTT GTA GCC ATT TTA GGA CGT CCC AAT GTT        48
Met Thr Phe Lys Ser Gly Phe Val Ala Ile Leu Gly Arg Pro Asn Val
 1               5                  10                  15

GGG AAG TCA ACC TTT TTA AAT CAC GTT ATG GGG CAA AAG ATT GCC ATC        96
Gly Lys Ser Thr Phe Leu Asn His Val Met Gly Gln Lys Ile Ala Ile
             20                  25                  30

ATG AGT GAC AAG GCG CAG ACA ACG CGC AAT AAA ATC ATG GGA ATT TAC       144
Met Ser Asp Lys Ala Gln Thr Thr Arg Asn Lys Ile Met Gly Ile Tyr
         35                  40                  45

ACG ACT GAT AAG GAG CAA ATT GTC TTT ATC GAC ACA CCA GGG ATT CAC       192
Thr Thr Asp Lys Glu Gln Ile Val Phe Ile Asp Thr Pro Gly Ile His
     50                  55                  60

AAA CCT AAA ACA GCT CTC GGA GAT TTC ATG GTT GAG TCT GCC TAC AGT       240
Lys Pro Lys Thr Ala Leu Gly Asp Phe Met Val Glu Ser Ala Tyr Ser
 65                  70                  75                  80

ACC CTT CGC GAA GTG GAC ACT GTT CTT TTC ATG GTG CCT GCT GAT GAA       288
Thr Leu Arg Glu Val Asp Thr Val Leu Phe Met Val Pro Ala Asp Glu
                 85                  90                  95

GCG CGT GGT AAG GGG GAC GAT ATG ATT ATC GAG CGT CTC AAG GCT GCC       336
Ala Arg Gly Lys Gly Asp Asp Met Ile Ile Glu Arg Leu Lys Ala Ala
            100                 105                 110

AAG GTT CCT GTG ATT TTG GTG GTG AAT AAA ATC GAT AAG GTC CAT CCA       384
Lys Val Pro Val Ile Leu Val Val Asn Lys Ile Asp Lys Val His Pro
        115                 120                 125

GAC CAG CTC TTG TCT CAG ATT GAT GAC TTC CGT AAT CAA ATG GAC TTT       432
Asp Gln Leu Leu Ser Gln Ile Asp Asp Phe Arg Asn Gln Met Asp Phe
    130                 135                 140

AAG GAA ATT GTT CCA ATC TCA GCC CTT CAG GGA AAT AAC GTG TCT CGT       480
Lys Glu Ile Val Pro Ile Ser Ala Leu Gln Gly Asn Asn Val Ser Arg
145                 150                 155                 160

CTA GTG GAT ATT TTG AGT GAA AAT CTG GAT GAA GGT TTC CAA TAT TTC       528
Leu Val Asp Ile Leu Ser Glu Asn Leu Asp Glu Gly Phe Gln Tyr Phe
                165                 170                 175
```

```
CCG TCT GAT CAA ATC ACA GAT CAT CCA GAA CGT TTC TTA GTT TCA GAA        576
Pro Ser Asp Gln Ile Thr Asp His Pro Glu Arg Phe Leu Val Ser Glu
        180                 185                 190

ATG GTT CGC GAG AAA GTC TTG CAC CTA ACT CGT GAA GAG ATT CCG CAT        624
Met Val Arg Glu Lys Val Leu His Leu Thr Arg Glu Glu Ile Pro His
        195                 200                 205

TCT GTA GCA GTA GTT GTT GAC TCT ATG AAA CGA GAC GAA GAG ACA GAC        672
Ser Val Ala Val Val Val Asp Ser Met Lys Arg Asp Glu Glu Thr Asp
        210                 215                 220

AAG GTT CAC ATC CGT GCA ACC ATC ATG GTC GAG CGC GAT AGC CAA AAA        720
Lys Val His Ile Arg Ala Thr Ile Met Val Glu Arg Asp Ser Gln Lys
225                 230                 235                 240

GGG ATT ATC ATC GGT AAA GGT GGC GCT ATG CTT AAG AAA ATC GGT AGT        768
Gly Ile Ile Ile Gly Lys Gly Gly Ala Met Leu Lys Lys Ile Gly Ser
                245                 250                 255

ATG GCC CGT CGT GAT ATC GAA CTC ATG CTA GGA GAC AAG GTC TTC CTA        816
Met Ala Arg Arg Asp Ile Glu Leu Met Leu Gly Asp Lys Val Phe Leu
                260                 265                 270

GAA ACC TGG GTC AAG GTC AAG AAA AAC TGG CGC GAT AAA AAG CTA GAT        864
Glu Thr Trp Val Lys Val Lys Lys Asn Trp Arg Asp Lys Lys Leu Asp
        275                 280                 285

TTG GCT GAC TTT GGC TAT AAT GAA AGA GAA TAC TAA                        900
Leu Ala Asp Phe Gly Tyr Asn Glu Arg Glu Tyr
        290                 295

(2) INFORMATION FOR SEQ ID NO:2:

(i) SEQUENCE CHARACTERISTICS:
        (A) LENGTH: 299 amino acids
        (B) TYPE: amino acid
        (D) TOPOLOGY: linear (ii) MOLECULE TYPE: protein (xi) SEQUENCE DESCRIPTION: SEQ ID NO:2:

Met Thr Phe Lys Ser Gly Phe Val Ala Ile Leu Gly Arg Pro Asn Val
  1               5                  10                  15

Gly Lys Ser Thr Phe Leu Asn His Val Met Gly Gln Lys Ile Ala Ile
                 20                  25                  30

Met Ser Asp Lys Ala Gln Thr Thr Arg Asn Lys Ile Met Gly Ile Tyr
             35                  40                  45

Thr Thr Asp Lys Glu Gln Ile Val Phe Ile Asp Thr Pro Gly Ile His
         50                  55                  60

Lys Pro Lys Thr Ala Leu Gly Asp Phe Met Val Glu Ser Ala Tyr Ser
 65                  70                  75                  80

Thr Leu Arg Glu Val Asp Thr Val Leu Phe Met Val Pro Ala Asp Glu
                 85                  90                  95

Ala Arg Gly Lys Gly Asp Asp Met Ile Ile Glu Arg Leu Lys Ala Ala
             100                 105                 110

Lys Val Pro Val Ile Leu Val Val Asn Lys Ile Asp Lys Val His Pro
         115                 120                 125

Asp Gln Leu Leu Ser Gln Ile Asp Asp Phe Arg Asn Gln Met Asp Phe
     130                 135                 140

Lys Glu Ile Val Pro Ile Ser Ala Leu Gln Gly Asn Asn Val Ser Arg
145                 150                 155                 160

Leu Val Asp Ile Leu Ser Glu Asn Leu Asp Glu Gly Phe Gln Tyr Phe
                 165                 170                 175

Pro Ser Asp Gln Ile Thr Asp His Pro Glu Arg Phe Leu Val Ser Glu
             180                 185                 190
```

Met Val Arg Glu Lys Val Leu His Leu Thr Arg Glu Glu Ile Pro His
    195                 200                 205

Ser Val Ala Val Val Asp Ser Met Lys Arg Asp Glu Glu Thr Asp
    210                 215                 220

Lys Val His Ile Arg Ala Thr Ile Met Val Glu Arg Asp Ser Gln Lys
225                 230                 235                 240

Gly Ile Ile Ile Gly Lys Gly Ala Met Leu Lys Lys Ile Gly Ser
                245                 250                 255

Met Ala Arg Arg Asp Ile Glu Leu Met Leu Gly Asp Lys Val Phe Leu
                260                 265                 270

Glu Thr Trp Val Lys Val Lys Lys Asn Trp Arg Asp Lys Lys Leu Asp
            275                 280                 285

Leu Ala Asp Phe Gly Tyr Asn Glu Arg Glu Tyr
290                 295

(2) INFORMATION FOR SEQ ID NO:3:

(i) SEQUENCE CHARACTERISTICS:
        (A) LENGTH: 900 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:3:

AUGACUUUUA AAUCAGGCUU UGUAGCCAUU UUAGGACGUC CCAAUGUUGG GAAGUCAACC        60

UUUUUAAAUC ACGUUAUGGG GCAAAAGAUU GCCAUCAUGA GUGACAAGGC GCAGACAACG       120

CGCAAUAAAA UCAUGGGAAU UUACACGACU GAUAAGGAGC AAAUUGUCUU UAUCGACACA       180

CCAGGGAUUC ACAAACCUAA AACAGCUCUC GGAGAUUUCA UGGUUGAGUC UGCCUACAGU       240

ACCCUUCGCG AAGUGGACAC UGUUCUUUUC AUGGUGCCUG CUGAUGAAGC GCGUGGUAAG       300

GGGGACGAUA UGAUUAUCGA GCGUCUCAAG GCUGCCAAGG UUCCUGUGAU UUUGGUGGUG       360

AAUAAAAUCG AUAAGGUCCA UCCAGACCAG CUCUUGUCUC AGAUUGAUGA CUUCCGUAAU       420

CAAAUGGACU UUAAGGAAAU UGUUCCAAUC UCAGCCCUUC AGGGAAAUAA CGUGUCUCGU       480

CUAGUGGAUA UUUUGAGUGA AAAUCUGGAU GAAGGUUUCC AAUAUUUCCC GUCUGAUCAA       540

AUCACAGAUC AUCCAGAACG UUUCUUAGUU UCAGAAAUGG UUCGCGAGAA AGUCUUGCAC       600

CUAACUCGUG AAGAGAUUCC GCAUUCUGUA GCAGUAGUUG UUGACUCUAU GAAACGAGAC       660

GAAGAGACAG ACAAGGUUCA CAUCCGUGCA ACCAUCAUGG UCGAGCGCGA UAGCCAAAAA       720

GGGAUUAUCA UCGGUAAAGG UGGCGCUAUG CUUAAGAAAA UCGGUAGUAU GGCCCGUCGU       780

GAUAUCGAAC UCAUGCUAGG AGACAAGGUC UUCCUAGAAA CCUGGGUCAA GGUCAAGAAA       840

AACUGGCGCG AUAAAAAGCU AGAUUUGGCU GACUUUGGCU AUAAUGAAAG AGAAUACUAA       900

(2) INFORMATION FOR SEQ ID NO:4:

(i) SEQUENCE CHARACTERISTICS:
        (A) LENGTH: 789 base pairs
        (B) TYPE: nucleic acid
        (C) STRANDEDNESS: single
        (D) TOPOLOGY: linear (ii) MOLECULE TYPE: DNA (genomic)

-continued (iii) HYPOTHETICAL: NO (iv) ANTI-SENSE: NO (xi) SEQUENCE DESCRIPTION: SEQ ID NO:4:

| | | | | | | |
|---|---|---|---|---|---|---|
| ATATCACGAC | GGAGCCATAC | TACCGATTTT | CTTAAGCATA | GCGCCACCTT | TACCGATGAT | 60 |
| AATCCCTTTT | TGGCTATCGC | GCTCGACCAT | GATGGTTGCA | CGGATGTGAA | CCTTGTCTGT | 120 |
| CTCTTCGTCT | CGTTTCATAG | AGTCAACAAC | TACTGCTACA | GAATGCGGAA | TCTCTTCACG | 180 |
| AGTTAGGTGC | AAGACTTTCT | CGCGAACCAT | TTCTGAAACT | AAGAAACGTT | CTGGATGATC | 240 |
| TGTGATTTGA | TCAGACGGGA | AATATTGGAA | ACCTTCATCC | AGATTTTCAC | TCAAAATATC | 300 |
| CACTAGACGA | GACACGTTAT | TTCCCTGAAG | GGCTGAGATT | GGAACAATTT | CCTTAAAGTC | 360 |
| CATTTGATTA | CGGAAGTCAT | CAATCTGAGA | CAAGAGCTGG | TCTGGATGGA | CCTTATCGAT | 420 |
| TTTATTCACC | ACCAAAATCA | CAGGAACCTT | GGCAGCCTTG | GAGACGCTCG | ATAATCATAT | 480 |
| CGTCCCCCTT | ACCACGCGCT | TCATCAGCAG | GCACCATGAA | AAGAACAGTG | TCCACTTCGC | 540 |
| GAAGGTACTG | TAGGCAGACT | CAACCATGAA | ATCTCCGAGA | GCTGTTTTAA | GTTTGTGAAT | 600 |
| CCCTGGTGTG | TCGATAAAGA | CAATTTGCTC | CTTATCAGTC | GTGTAATTCC | CATGATTTTA | 660 |
| TTGCGCGTTG | TCTGCGCCTT | GTCACTCATG | ATGGCAATCT | TTTGCCCCAT | AACGTGATTT | 720 |
| AAAAAGGTTG | ACTTCCCAAC | ATTGGGACTC | CTAAAATGGC | TACAAACCTG | ATTTAAAATT | 780 |
| CATAATTCC | | | | | | 789 |

We claim:

1. An isolated nucleic acid compound encoding the protein of SEQ ID NO:2.

2. An isolated nucleic acid compound, wherein the sequence of said compound is selected from the group consisting of:
   (a) SEQ ID NO:1;
   (b) SEQ ID NO:3; and
   (c) a nucleic acid compound fully complementary to (a) or (b).

3. An isolated nucleic acid compound, wherein the sequence of said compound is SEQ ID NO:4.

4. An isolated nucleic acid compound of claim 2 wherein the sequence of said compound is SEQ ID NO:1 or a sequence fully complementary to SEQ ID NO:1.

5. An isolated nucleic acid compound of claim 2 wherein the sequence of said compound is SEQ ID NO:3 or a sequence fully complementary to SEQ ID NO:3.

6. An isolated nucleic acid compound that hybridizes to SEQ ID NO:1 under high stringency conditions.

7. A vector comprising an isolated nucleic acid compound of claim 2.

8. A vector, as in claim 7 wherein said isolated nucleic acid compound is SEQ ID NO:1, operably-linked to a promoter sequence.

9. A host cell containing a vector of claim 7.

10. A host cell containing a vector of claim 8.

11. A method for constructing a recombinant host cell that expresses SEQ ID NO:2, said method comprising introducing into said host cell by any suitable means a vector of claim 8.

12. A method for expressing SEQ ID NO:2 in the recombinant host cell of claim 11 said method comprising culturing said recombinant host cell under conditions suitable for gene expression.

* * * * *